(12) United States Patent
Maddry (10) Patent No.: US 10,231,851 B2
(45) Date of Patent: Mar. 19, 2019

(54) PNEUMATIC ELECTROMYOGRAPHIC EXOSKELETON

(71) Applicant: Conor J. Maddry, Great Falls, VA (US)

(72) Inventor: Conor J. Maddry, Great Falls, VA (US)

( * ) Notice: Subject to any disclaimer, the term of this patent is extended or adjusted under 35 U.S.C. 154(b) by 689 days.

(21) Appl. No.: 14/830,348

(22) Filed: Aug. 19, 2015

(65) Prior Publication Data

US 2016/0058647 A1  Mar. 3, 2016

Related U.S. Application Data (60) Provisional application No. 62/043,745, filed on Aug. 29, 2014.

(51) Int. Cl.
| | |
|---|---|
| A61F 2/68 | (2006.01) |
| A61H 1/02 | (2006.01) |
| A61H 3/00 | (2006.01) |
| B25J 9/00 | (2006.01) |
| A61B 5/0488 | (2006.01) |

(52) U.S. Cl.
CPC .............. *A61F 2/68* (2013.01); *A61B 5/0488* (2013.01); *A61H 1/024* (2013.01); *A61H 1/0244* (2013.01); *A61H 1/0266* (2013.01); *A61H 1/0277* (2013.01); *A61H 1/0281* (2013.01); *A61H 3/00* (2013.01); *B25J 9/0006* (2013.01); *A61H 2201/1238* (2013.01); *A61H 2201/164* (2013.01); *A61H 2201/165* (2013.01); *A61H 2201/1614* (2013.01); *A61H 2201/1619* (2013.01); *A61H 2201/1623* (2013.01); *A61H 2201/1628* (2013.01); *A61H 2201/1635* (2013.01); *A61H 2201/5071* (2013.01); *A61H 2230/605* (2013.01)

(58) Field of Classification Search
None
See application file for complete search history.

(56) References Cited

U.S. PATENT DOCUMENTS

| | | | | |
|---|---|---|---|---|
| 3,735,425 A | * | 5/1973 | Hoshall | A61B 5/0428 623/25 |
| 5,112,296 A | * | 5/1992 | Beard | A61F 5/0113 128/905 |
| 6,238,338 B1 | * | 5/2001 | DeLuca | A61B 5/681 128/903 |

(Continued)

*Primary Examiner* — Sundhara M Ganesan
(74) *Attorney, Agent, or Firm* — Hunton Andrews Kurth LLP (57) ABSTRACT

The invention relates to a pneumatic, electromyographic exoskeleton. The exoskeleton includes a rigid frame designed to be secured to at least a portion of a user's body, a number of pneumatic actuators, each fixed to opposite sides of a hinge on the rigid frame; a storage tank designed to store compressed air to power the pneumatic actuators; valves coupled to the pneumatic actuators to control activation of the pneumatic actuators; electromyographic (EMG) sensors for sensing EMG signals in skeletal muscles of the user; differential amplifiers for amplifying each EMG signal to generate an amplified EMG signal; and a microprocessor programmed to receive the amplified EMG signals and to output activation signals for the pneumatic actuators.

8 Claims, 4 Drawing Sheets

(56) References Cited

U.S. PATENT DOCUMENTS

| | | | | |
|---|---|---|---|---|
| 6,511,442 B1* | 1/2003 | Lathan | | A61B 5/16 600/595 |
| 8,419,804 B2* | 4/2013 | Herr | | A61F 2/60 623/24 |
| 8,945,028 B2* | 2/2015 | Kazerooni | | A61H 3/00 601/23 |
| 9,808,390 B2* | 11/2017 | Caires | | A61H 3/00 |
| 2004/0267331 A1* | 12/2004 | Koeneman | | A61H 1/02 607/49 |
| 2006/0189899 A1* | 8/2006 | Flaherty | | A61B 5/0476 600/595 |
| 2008/0009771 A1* | 1/2008 | Perry | | B25J 9/0006 600/587 |
| 2009/0319054 A1* | 12/2009 | Sankai | | A61B 5/04888 623/25 |
| 2010/0256537 A1* | 10/2010 | Menga | | B25J 9/0006 601/34 |
| 2010/0280628 A1* | 11/2010 | Sankai | | A61B 5/04888 623/25 |
| 2010/0324699 A1* | 12/2010 | Herr | | A61F 2/66 623/27 |
| 2011/0266323 A1* | 11/2011 | Kazerooni | | B25J 9/0006 224/575 |
| 2012/0172770 A1* | 7/2012 | Almesfer | | B25J 9/0006 601/35 |
| 2014/0148725 A1* | 5/2014 | Cadwell | | A61B 5/04001 600/546 |
| 2014/0212243 A1* | 7/2014 | Yagi | | A61H 3/00 414/2 |
| 2014/0276265 A1* | 9/2014 | Caires | | A61H 3/00 601/34 |
| 2015/0005585 A1* | 1/2015 | Xu | | A61B 5/0402 600/300 |
| 2015/0045689 A1* | 2/2015 | Barone | | A61B 5/0004 600/546 |
| 2015/0088025 A1* | 3/2015 | Litvak | | A61B 5/0488 600/546 |
| 2015/0134080 A1* | 5/2015 | Roh | | B25J 9/0006 623/32 |
| 2015/0173993 A1* | 6/2015 | Walsh | | A61H 1/024 414/4 |
| 2015/0289995 A1* | 10/2015 | Wilkinson | | B25J 19/0091 623/27 |

* cited by examiner

PNEUMATIC ELECTROMYOGRAPHIC EXOSKELETON

CROSS-REFERENCE TO RELATED APPLICATIONS

This application claims priority to Provisional Application No. 62/043,745, filed Aug. 29, 2014, which is hereby incorporated by reference in its entirety.

FIELD OF THE INVENTION

The invention relates generally to a support structure for a human body, and more particularly to an exoskeleton that uses eletromyographic sensors and pneumatic actuators.

BACKGROUND

Various efforts have been made to construct an apparatus worn by a human that enhances the wearer's ability to carry out certain tasks, such as lifting heavy objects, walking long distances, or climbing. Exoskeletons of different forms have been built and tested. However, most have a number of drawbacks such as a requirement to be connected to the electric power grid, a lack of precision in sensing when to activate a joint, and excessive weight. Consequently, exoskeletons have not enjoyed widespread use or acceptance. At the same time, there are increasing needs and applications for a body apparatus that can reliably enhance a user's strength and that is not overly constrictive in terms of weight or power supply requirements. It would advantageous, therefore, to have an exoskeleton that overcame one or more of the aforementioned drawbacks.

SUMMARY

According to one embodiment, the invention relates to a pneumatic, electromyographic exoskeleton. The exoskeleton includes a rigid frame designed to be secured to least a portion of a user's body, a number of pneumatic actuators, each fixed to opposite sides of a hinge on the rigid frame; a storage tank designed to store compressed air to power the pneumatic actuators; valves coupled to the pneumatic actuators to control activation of the pneumatic actuators; electromyographic (EMG) sensors for sensing EMG signals in skeletal muscles of the user; differential amplifiers for amplifying each EMG signal to generate an amplified EMG signal; a microprocessor programmed to receive the amplified EMG signal, detect whether the amplified EMG signal is outside of a threshold voltage region, detect whether the amplified EMG signal has been within the threshold voltage region for a defined delay period, and output an activation signal for a pneumatic actuator beginning when the amplified EMG signal is outside the threshold voltage region and ending when the amplified EMG signal has remained within the threshold voltage region for the predetermined delay period. Each activation signal is received by one of the valves, and the activation signal opens the valve to cause pressurized air from the storage tank to activate the pneumatic actuator thereby causing a rotation of the rigid frame to enhance the user's strength.

According to a preferred embodiment of the invention, the exoskeleton does not need to be connected to the power grid, which greatly enhances its usefulness. It can also be designed to be of an acceptable weight so that it can be worn for an extended period of time. The EMG circuit and signal processing circuit can also provide the advantage of reliably sensing the user's muscle signals and smoothing such signals to provide a stable and consistent activation of the pneumatic actuators.

The exoskeleton can be useful in a number of applications. It may be used in military applications to assist the user in lifting heavy objects or making long distance hikes less rigorous. It may also be used in hospitals for rehabilitation and the transport of patients. There are also applications with elderly people as well as people with muscular disabilities who have trouble walking or lifting heavy objects.

BRIEF DESCRIPTION OF THE DRAWINGS

In order to facilitate a fuller understanding of the present invention, reference is now made to the attached drawings. The drawings should not be construed as limiting the present invention, but are intended only to illustrate different aspects and embodiments of the invention.

DETAILED DESCRIPTION

Figure 1:
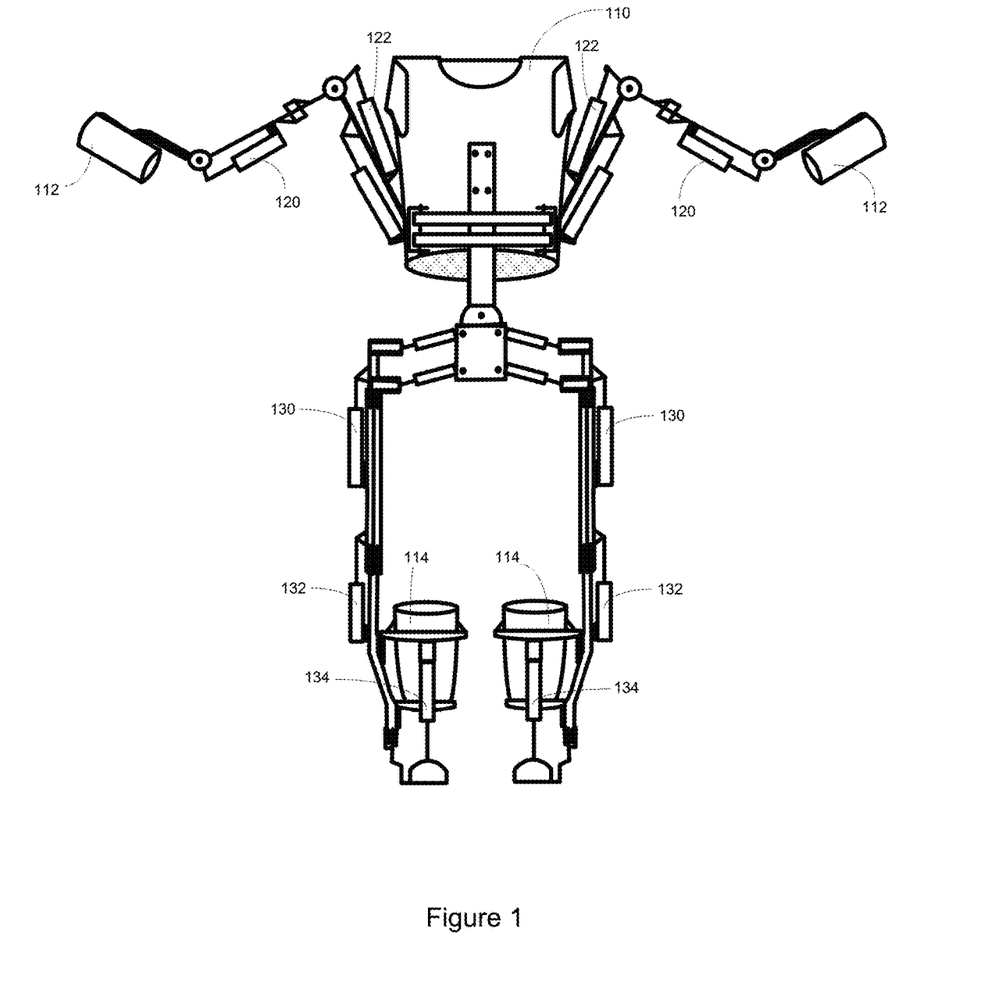
FIG. 1 is a drawing of a full-body, pneumatic, electromyographic exoskeleton according to one embodiment of the invention.

FIG. 1 is a drawing of a full-body pneumatic, electromyographic exoskeleton frame according to one embodiment of the invention. The exoskeleton is preferably a full body system that amplifies the movement of fourteen muscles when operating at is full capacity. As shown in FIG. 1, the exoskeleton frame may include a rigid torso housing 110, forearm housing 112, and calf housing 114 which are secured around these portions of the user's body when in operation. The housing portions are effective to securely fix the exoskeleton frame to the user such that the actuators can exert forces on different joints of the body when the corresponding muscle is flexed.

FIG. 1 also depicts a number of rigid frame members that are secured to the housings and also to the pneumatic actuators. The rigid frame members can be formed using a rigid material such as aluminum or carbon fiber, for example.

A number of pneumatic actuators are also shown in FIG. 1. The pneumatic actuators receive pressurized air from a storage tank and are activated when the user flexes his or her corresponding muscle, such that the actuators enhance the user's strength. In the example shown in FIG. 1, there are ten different pneumatic actuators. Some or all of the pneumatic actuators may be dual-action actuators that can be activated to contract and also to expand. This feature is useful for some joints such as the elbow joint where the actuator can assist the user both in extending the arm (e.g. to assist the tricep) and retracting the arm (e.g., to assist the bicep).

As shown in FIG. 1, the exoskeleton may include a pneumatic actuator 120 for the elbow joint, actuator 122 for the shoulder, actuator 130 for the hip, actuator 132 for the knee, and actuator 134 for the ankle.

The frame shown in FIG. 1 is preferably designed so that all or nearly all of the force from each pneumatic actuator is transferred into torque around the applicable joint. The back plate shown in FIG. 1 can be designed to support all of the electronic and pneumatic systems. The back plate can also be fitted with a joint at the bottom that replicates the movement of the hip so that the wearer can maintain nearly full mobility. The frame structure for the user's arms is preferably designed so that the user's arms can move on many axes of motion. For example, a joint can be created off of the back plate that can rotate on four axes in order to maintain as much maneuverability as possible. Off of this joint the elbow can be attached and braces can be made to branch off of the arm in two places.

The frame can be fitted with the ten pneumatic actuators (five on each side) and those actuators can be wired into the back plate that contains two manifolds, each including seven 3-way valves.

Figure 2:
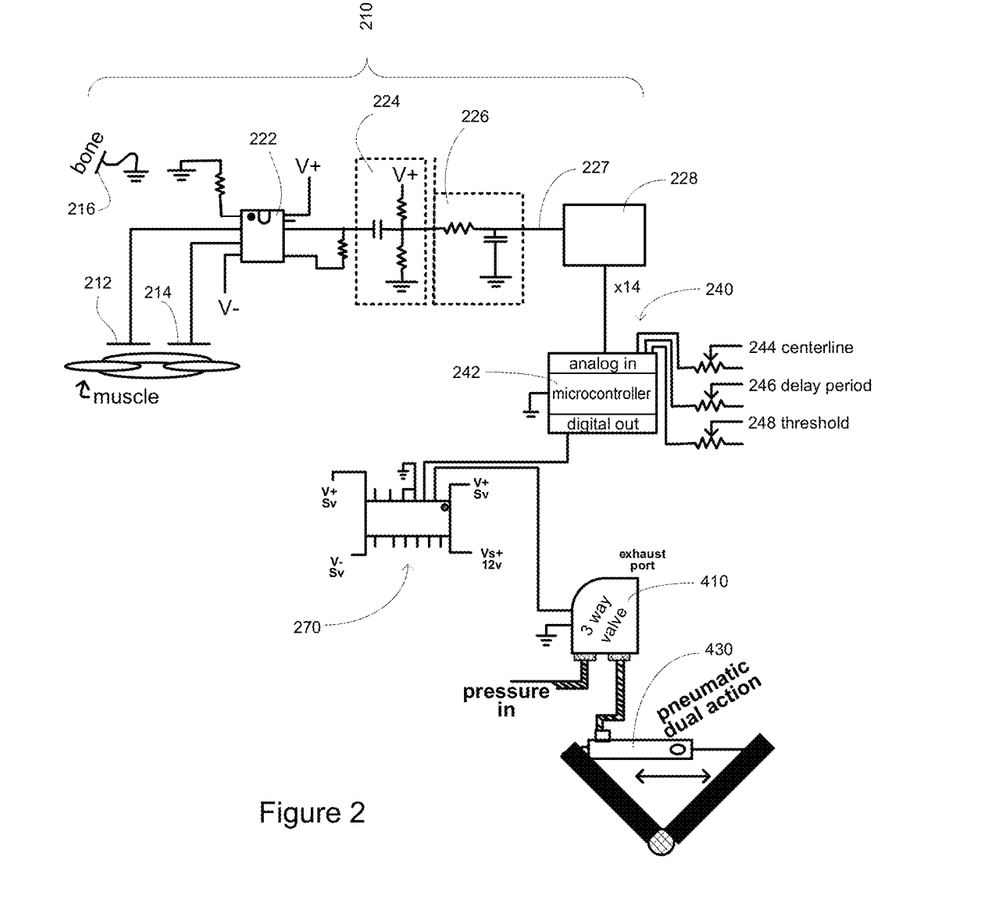
FIG. 2 is a diagram of an electromyographic circuit, a signal processing circuit, and a valve driver circuit according to one embodiment of the invention.

FIG. 2 is a diagram of an electrical system for the exoskeleton according to an exemplary embodiment of the invention. As shown in FIG. 2, the electrical system comprises three main components. The first component is the electromyography (EMG) circuit 210. The second component is the signal processing circuit 240. The third component is the valve driver circuit 270. The EMG circuit 210 senses the electrical signals in the user's muscles, amplifies the signals, and filters out high frequency noise. The signal processing circuit 240 receives the amplified signals from the EMG circuit and applies an algorithm that produces a digital output signal that has been smoothed using a threshold value, a centerline value, and a delay value. The valve driver circuit 270 receives the digital output signals from the signal processing circuit 240 and uses them to drive the valves controlling the pneumatic actuators on the exoskeleton frame.

According to one embodiment of the invention, the full body exoskeleton includes fourteen sets of sensors and actuators, each set sensing the contraction of a particular muscle and activating a pneumatic actuator applied to the corresponding joint. The sensors are applied to the user's calves, quadriceps, hip flexors, biceps, triceps, lats (latissimus dorsi), and traps (trapezius), and the pneumatic actuators are applied, respectively, to the user's ankle, knee, hip, elbow (for flexion and extension), and shoulder (to lower and raise). The pneumatic actuators can be dual action (bi-directional) so that they can be actuated to expand and to contract. For simplicity, the circuit illustrated in FIG. 2 depicts only one such set, and the following description will use a bicep and flexion of the elbow joint as an example to illustrate the operation of the invention.

Figure 5:
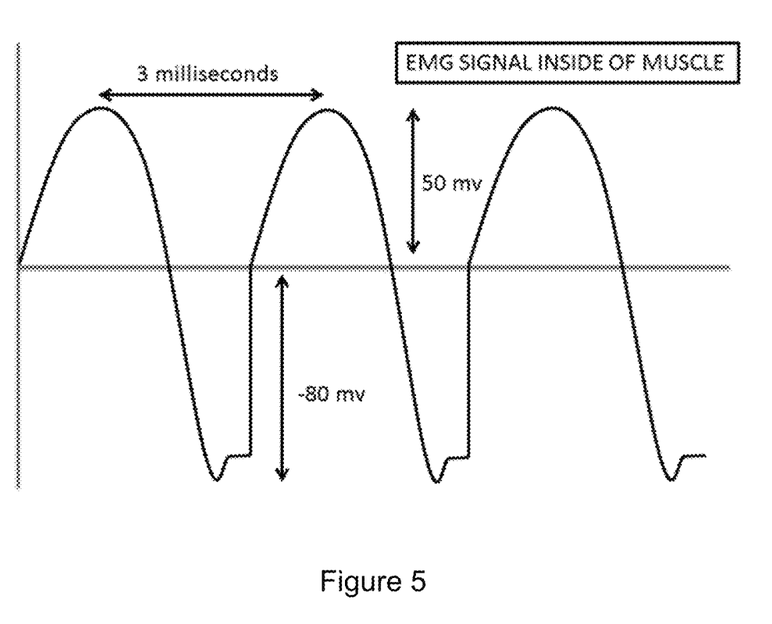
FIG. 5 shows an example of the general shape and magnitude of an electrical signal within a skeletal muscle.

As shown in FIG. 2, there are typically three sensors for each muscle. Using the bicep as an example, the first sensor 212 is applied to one end of the bicep, the second sensor 214 is applied to the other end of the bicep, and the third sensor 216 is applied to a grounding location such as proximate to the ulna (elbow bone). When the user flexes his or her bicep, electrical signals are transmitted through the bicep. An example of the general shape and magnitude of signals travelling through a muscle is shown in FIG. 5.

The purpose of the EMG circuit 210 is to detect the signal travelling through the muscle with the sensors 212, 214 affixed to the user's skin, and to amplify the signal so it can be read by the microprocessor. The EMG circuit 210 includes the muscle sensors 212, 214, the ground sensor 216, and a differential amplifier 222 that receives the signals detected by the sensors 212, 214. The first sensor 212 is connected to one input of the differential amplifier 222, and the second sensor 214 is connected to the second input of the differential amplifier 222. The ground sensor 216 and one of the contacts of the differential amplifier 222 are both connected to a common ground. The differential amplifier 222, which may be a INA106 amplifier manufactured by Texas Instruments, for example, detects the difference in voltage between the two input signals from the sensors 212, 214 and amplifies the voltage by a predetermined multiplier.

According to one embodiment, the output of the differential amplifier 222 is wave roughly in the shape of a sine wave having an amplitude of about 1-2 millivolts (mV) and a period of about 1-2 milliseconds (mS). There are two reasons for the oscillation and irregularity of this wave. First, the actual electrical signal within the muscle when it is flexed is not a constant voltage. It may vary between about 50 mV and about −80 mV, as shown in FIG. 3. Second, because the electrodes 212, 214 are on the surface of the user's skin, they pick up a much smaller amount of the electrical signal from the muscle. These characteristics of the muscle signal and sensor location typically leave gaps in the detected signal (and in the signal output from the differential amplifier 222) when the muscle is being flexed.

Because the output of the differential amplifier 222 varies between approximately +1 millivolt and −1 millivolt, a voltage divider 224 is provided, according to one embodiment of the invention, so that the wave is entirely in the positive voltage range, as opposed to partially positive and partially negative. The voltage divider 224 receives the varying signal from the differential amplifier 222 and shifts it in a positive voltage direction so that it varies between about 0 and 2 mV.

The output of the voltage divider 224 is connected to a low pass filter 226 as shown in FIG. 2. The low pass filter 226 comprises a capacitor and resistor. According to one embodiment, the resistor has a value of 33 ohms ($\Omega$) and the capacitor has a capacitance of 4.7 microfarads ($\mu$F), which results in significant attenuation of signal frequencies above about 660 hertz (Hz).

Figure 3A:
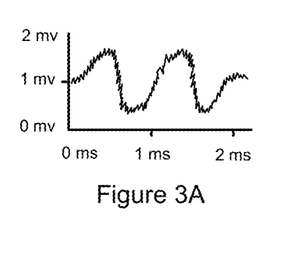
FIG. 3A shows a signal from a skeletal muscle that has amplified according to one embodiment of the invention.

As a result of the amplification, upward positive bias, and low pass filtering provided by the EMG circuit 210, the output signal of the EMG circuit 210 can be read much more reliably by the signal processing circuit 240 and further refined to power the pneumatic actuators at the appropriate times. An example of the signal output from the EMG circuit 210 (measured at point 227 on FIG. 2) is shown in FIG. 3A. As illustrated in FIG. 3A, the signal appears generally sinusoidal with a period of about 1-2 milliseconds and an amplitude of about 1-2 millivolts. Although still a relatively small signal, it is sufficiently large and regular as to provide a very useful signal for indicating when the muscle is being flexed. This in turn allows the appropriate pneumatic actuator on the exoskeleton to be powered at the appropriate time to augment the power provided by the muscle at the applicable joint, e.g., allowing the pneumatic actuator for the elbow joint to be activated simultaneously with the user's contraction of the bicep muscle. Hence, the EMG circuit is able to detect, amplify, bias, and filter high frequency noise from, the muscle signal. The EMG circuit 210 outputs a signal that can be reliably detected at an analog input of the signal processing circuit 240.

According to another embodiment of the invention, an additional amplifier can be provided in the EMG circuit 210 to further enhance the utility of the signal detected by the sensors 212, 214. As shown in FIG. 2, the second amplifier 228 can be added between the output of the low pass filter 226 and the input of the signal processing circuit 240. According to one example, the second amplifier 228 may comprise a LM386 linear audio amplifier manufactured by Texas Instruments and having a gain of about 200. The second amplifier 228 further amplifies the voltage signal to enable enhanced reliability in processing of the signal by the signal processing circuit 240.

The signal processing circuit 240, which comprises a microprocessor 242 and associated electrical connectors, receives the analog output from the EMG circuit 210. The microprocessor 242 may be any suitable computer processor, such as an Arduino™ Mega processor, for example. A breakout board can also be included in the signal processing circuit 240 to facilitate connection to the inputs to and outputs from the microprocessor 242. According to one embodiment, the breakout board uses pins that connect into the inputs of the Arduino™ Mega microprocessor. Those pins can be connected to a ribbon cable that carries input signals from the EMG circuit 210 to the microprocessor 242, and from the microprocessor 242 to a number of jumper wires that send digital output signals from the microprocessor 242 to the valve driver board 270.

Figure 4:
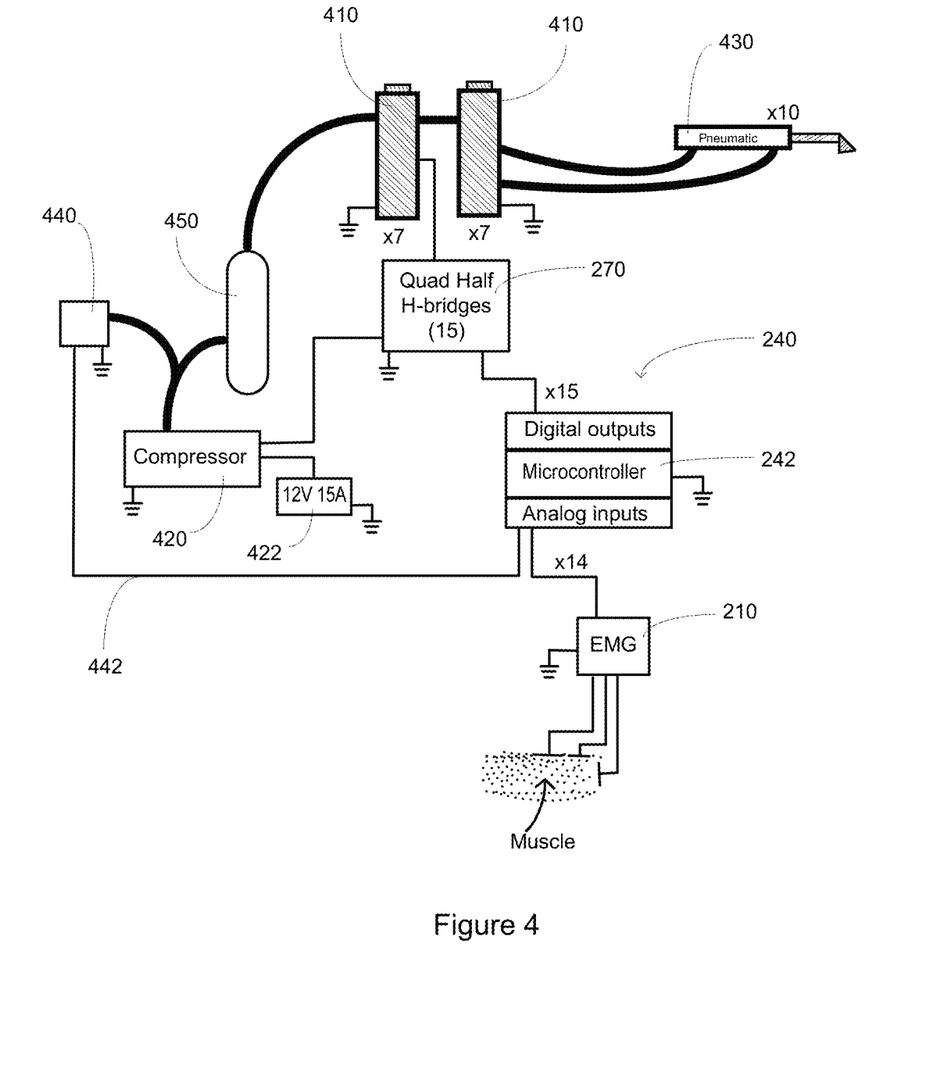
FIG. 4 shows a pneumatic system of the exoskeleton according to an exemplary embodiment of the invention.

The microprocessor 242 can be programmed to process the input signal from the EMG circuit 210 before it is applied to actuate the pneumatic actuator. As described above, the electrical signal in the user's bicep can be somewhat erratic. Hence, if it were used directly to actuate the pneumatic actuator 430, the pneumatic actuator could be powered on and off at a high and irregular frequency. Accordingly, signal processing can be used to modify the characteristics of the signal so that it is much more suitable to actuating the pneumatic actuator in a controlled manner. In particular, to counteract the rapid pulsing of the muscle signal described above, the code used by the microprocessor 242 for interpreting the signal from the EMG circuit 210 can be designed so that it takes into account the oscillating nature of the muscle signal as well as the short duration loss of signal that may occur when the muscle is still being flexed due to the location of the sensors on the skin and not directly in the muscle. The signal processing can be achieved by programming the microprocessor 242 to read the input signal from the EMG circuit 240 and to output a signal that has been smoothed and regulated to accommodate these physiological characteristics of the system.

Because of the sensors' non-stable output when the muscle is being flexed, the code can be written to compensate for the gaps in the voltage coming to the analog input of the microprocessor 242. According to one embodiment of the invention, the microprocessor 242 has an input "unit value" that is correlated to and proportional to the value of the input voltage. For example, the input unit value of the microprocessor 242 may range from 0 to 1023 which may correspond to an input voltage value of 0 to 40 millivolts. In this example, an input voltage ranging from 0-2 millivolts would correspond to an input unit value of about 0 to 50 units.

After the range of input units has been established (e.g., 0-50 input units corresponding to 0-2.0 millivolts), then three parameters can be defined to achieve the smoothing function. The first parameter is the centerline voltage when the muscle is at rest (i.e., not flexing). The second parameter is the threshold voltage, defined as a voltage difference between the centerline and a voltage value above and below the centerline. The third parameter is the delay value. These values can be hard-coded in the program code running on the microprocessor 242. However, it is usually advantageous to include a trimmer (e.g., potentiometer) for each parameter so that they can each be adjusted manually to optimize the effectiveness of the signal processing circuit 240. FIG. 2 illustrates a first trimmer 244 to adjust the centerline voltage, a second trimmer 246 to adjust the delay period, and a third trimmer 248 to adjust the value of the threshold voltage.

Before the EMG signal can be analyzed, the centerline voltage of each individual electromyographic channel is determined. The centerline voltage is determined by finding the signal voltage of the muscle when it is not being flexed. The unit value corresponding to the relaxed position of each muscle is assigned as the centerline voltage and the two thresholds (above and below the centerline) for each channel are calculated off of that value.

Figure 3B:
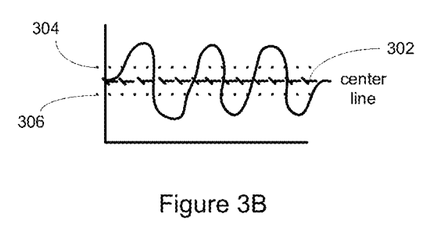
FIG. 3B shows an amplified, filtered signal in relation to a centerline voltage, defined threshold values, and a delay period according to one embodiment of the invention.

If the input range of the signal is 0-50 units, typically the threshold value would be set at about 5-10 input units (corresponding to 0.2-0.4 millivolts). The threshold value is used to determine if the muscle is being flexed, which serves as a trigger to activate the pneumatic actuator. FIG. 3B shows an example of the threshold values that may be established for a typical wave form. The line 302 is the centerline voltage. The line 304 is the threshold value above the centerline voltage. The line 306 is the threshold value below the centerline voltage. In this example, when the muscle is first flexed, the input unit value may jump by about 20-50 units. At that point, the output signal is turned on (High), and the time of the initial contraction is set. The output signal High value may be set as a digital 5 volt signal output from the microprocessor 242, for example.

As the code cycles through again and measures the analog input signal, if the analog input signal (from the output of the EMG circuit 210) is no longer greater than the upper threshold value 304 (e.g., 10 units above the centerline) or less than the lower threshold value 306 (i.e., no longer outside of the region defined by the upper and lower threshold values 304, 306), the output signal will continue to stay on (High) until a preset delay period, e.g., 140 milliseconds, has elapsed. The inventor determined that while the muscle is being flexed, the periods during which the signal stays within the threshold values 304, 306 (e.g., within 10 units of the centerline 302) is typically less than a determinable delay period (e.g., 140 milliseconds). Accordingly, by the time the signal from the EMG circuit 210 read by the microprocessor 242 reaches outside of the threshold value region again, the output from the microprocessor 242 is already on and then continues to stay on. Hence, the output signal from the microprocessor 242 has been stabilized and does not flicker as the corresponding muscle is flexed. As a result, the pneumatic actuator is activated during the entire period when the muscle is being flexed and does not have any gaps.

The trimmers 244 (centerline), 246 (delay), and 248 (threshold) can allow the user to fine tune the signal processing circuit 240 to stabilize the output of the signal processing circuit 240 so that it is on and stable during muscle flexing and otherwise off. For example, the threshold trimmer 244 may allow the user to adjust the threshold between 0 and 40 units, and the delay trimmer 246 may allow the user the adjust the delay period to values between 100 and 600 milliseconds. Other values for the threshold value and delay period can be used in order to tune the signal processing circuit 240 for a specific application. The centerline trimmer 244 allows the user to adjust the centerline to be an equal voltage amount away from the peaks and troughs of the input wave signal.

The digital output signal from the microprocessor 242 is transmitted to a valve driver circuit 270 as shown in FIG. 2. The valve driver circuit 270 comprises four quad half H-bridges according to an exemplary embodiment of the invention. Each H-bridge comprises four power transistors. The first transistor is activated by the 5-volt logic signal output from the microprocessor 242, and the output signal from the first transistor activates the second transistor. The second transistor includes a power source and it has an output signal that is large enough to power the valves, which may include a solenoid requiring a much higher voltage and current than what is output by the microprocessor 242. Each of the H-bridges controls four individual valves by either turning them on or off. The outputs of the H-bridges connect into the two manifolds 410 giving the microprocessor 242 control over the valves. The outputs of the H-bridges open the valves, which releases pressurized air into the appropriate pneumatic actuator to cause it to extend or contract, depending on the joint. In the bicep example, the pressurized air is released into the pneumatic actuator to make it contract, which decreases the angle between the upper arm and forearm.

According to one embodiment, in the full body exoskeleton, the EMG circuit 210 contains fourteen differential amplifiers 222 that connect to the 29 electrodes (2 per amplifier plus one ground) through two D-sub connectors. This EMG circuit board 210 is connected to a breakout board for the signal processing circuit 240 by a ribbon cable. The ribbon cable takes all of the output of all of the sensors and sends them to the analog inputs of the microprocessor 242 along with supplying the board with + and −9 volts.

Referring to FIG. 4, the pneumatic system will now be described. The pneumatic system, according to one embodiment, comprises fourteen three-way valves in a valve manifold 410, a 1.5 cubic feet per minute (cfm) compressor 420 powered by a 12-volt rechargeable battery 422, ten double-acting pneumatic actuators 430, a pneumatic pressure sensor 440, and a pressure tank 450. The entire system can operate effectively between a pressure of 30 and 90 psi, for example.

The pneumatic pressure sensor 440 is wired into the analog input of the microcontroller 242. The signal transmitted by the pressure sensor 440 to the microcontroller along the line 442 represents the pressure in the tank 450 and is typically between 0 and 10 volts, which corresponds to a pressure between 0 and 120 pounds per square inch (psi). A threshold pressure value can be set using the microprocessor 242 such that when the pressure in the tank 450 falls below the threshold, the microprocessor 242 sends a command to the compressor to turn on, thus increasing the pressure in the tank 450. According to one example, the threshold is set to a value between 3 and 10 volts, which corresponds to a pressure value between 30 and 100 psi. When the pressure sensor reads any psi lower than the threshold value, it turns on the compressor via a quad half H-bridge 270 that is wired to the digital output of the microcontroller 242. This maintains the pressure at the desired amount even when some of the air is being depleted because of the pneumatic actuators being triggered. The compressor 420 pressurizes air in the tank 450. To keep the overall weight of the exoskeleton relatively light, the tank 450 may be designed to be relatively small, e.g., having a volume that is approximately the same volume as 4-8 of the actuators. The compressor 420 can refill the volume of two triggered pneumatic actuators in one second, according to one example, so the pressure in the tank 450 is never fully depleted. The tank 450 is connected to the two seven-valve manifolds 410, and each valve is connected to its respective pneumatic actuator 430. One desirable feature of the entire system is for the air pressure to be easily and rapidly replenished and for the entire system to be portable so it can easily be worn with minimal strain on the user.

The exoskeleton also includes a power distribution system. The power distribution system includes a power distribution board according to a preferred embodiment of the invention. The power distribution board receives a 12-volt input from a battery (e.g., similar to a batter for a portable drill) and splits the 12-volt input into a regulated 12-volt output and a regulated 5-volt output, according to one embodiment of the invention. The 12-volt output powers the microprocessor 242 and the valves in the manifold 410. The 5-volt output powers the logic supply for the valve driver board 270, the pneumatic pressure sensor 440, and the enable pins of the valve driver board 270.

One advantage that various embodiments of the invention can provide is a self-powered exoskeleton that does not need to be connected to the power grid, which greatly enhances its usefulness. It can also be designed to be of an acceptable weight so that it can be worn for an extended period of time. The EMG circuit and signal processing circuit can also provide the advantage of reliably sensing the user's muscle signals and smoothing such signals to provide a stable and consistent activation of the pneumatic actuators.

The exoskeleton can be useful in a number of applications. It could be used in military applications to assist the user in lifting heavy objects or making long distance hikes less rigorous. It could also be used in hospitals for rehabilitation and the transport of patients. There are also applications with elderly people as well as people with muscular disabilities who have trouble walking or lifting heavy objects. It may also assist disabled people who would otherwise be unable to walk.

As described above, the signal processing circuit 240 in FIG. 1 may include at least one programmed processor and at least one memory or storage device. The memory may store a set of instructions. The instructions may be either permanently or temporarily stored in the memory or memories of the processor. The set of instructions may include various instructions that perform a particular task or tasks, such as those tasks described above. Such a set of instructions for performing a particular task may be characterized as a program, software program, or simply software.

The microprocessor 242 in FIG. 1 may include software or computer programs stored in the memory (e.g., non-transitory computer readable medium containing program code instructions executed by the processor) for executing the methods described herein. The set of instructions may be in the form of a program or software. The software may be in the form of system software or application software, for example. The software may also be in the form of a collection of separate programs, a program module within a larger program, or a portion of a program module, for example. The software instructs the processor what to do with the data being processed.

Further, it is appreciated that the instructions or set of instructions used in the implementation and operation of the invention may be in a suitable form such that the processor 242 may read the instructions. For example, the instructions that form a program may be in the form of a suitable programming language, which is converted to machine language or object code to allow the processor or processors to read the instructions. That is, written lines of programming code or source code, in a particular programming language, are converted to machine language using a compiler, assembler or interpreter. The machine language is binary coded machine instructions that are specific to a particular type of processor, i.e., to a particular type of computer, for example. Any suitable programming language may be used in accordance with the various embodiments of the invention. For example, the programming language used may include assembly language, Ada, APL, Basic, C, C++, COBOL, dBase, Forth, Fortran, Java, Modula-2, Pascal, Prolog, REXX Visual Basic, and/or JavaScript. Further, it is not necessary that a single type of instructions or single programming language be utilized in conjunction with the operation of the system and method of the invention. Rather, any number of different programming languages may be utilized as is necessary or desirable.

Although the embodiments of the present invention have been described herein in the context of a particular implementation in a particular environment for a particular purpose, those skilled in the art will recognize that its usefulness is not limited thereto and that the embodiments of the present invention can be beneficially implemented in any number of environments for any number of purposes.

What is claimed is:

1. A pneumatic, electromyographic exoskeleton comprising:
    a rigid frame designed to be secured to least a portion of a body of a user, the rigid frame comprising a plurality of hinges corresponding to joints of the user;
    a plurality of pneumatic actuators, each pneumatic actuator being fixed to opposite sides of a hinge on the rigid frame, wherein at least some of the pneumatic actuators are dual-action pneumatic actuators;
    a storage tank designed to store compressed air to power the pneumatic actuators, wherein a volume of the storage tank is less than a combined volume of the plurality of pneumatic actuators;
    a compressor connected to the storage tank for pumping compressed air into the storage tank;
    a pneumatic pressure sensor connected to the storage tank for sensing a pressure in the storage tank;
    a plurality of valves coupled to the pneumatic actuators to control activation of the pneumatic actuators, wherein the valves coupled to the dual-action pneumatic actuators comprise 3-way valves;
    a plurality of electromyographic (EMG) sensors for sensing EMG signals in skeletal muscles of the user, each EMG sensor comprising a first contact pad and a second contact pad for sensing an EMG signal in a skeletal muscle of the user and a differential amplifier for amplifying the EMG signal to generate an amplified EMG signal;
    a microprocessor programmed to:
        receive the amplified EMG signal;
        detect whether the amplified EMG signal is outside of a threshold voltage region;
        detect whether the amplified EMG signal has been within the threshold voltage region for a defined delay period; and
        output an activation signal for a pneumatic actuator beginning immediately after the amplified EMG signal is outside the threshold voltage region and ending when the amplified EMG signal has remained within the threshold voltage region for the predetermined delay period; and
    wherein the activation signal is received by one of the valves, and the activation signal opens the value to cause pressurized air from the storage tank to activate the pneumatic actuator thereby causing a rotation of the rigid frame about an axis of the hinge; and
    wherein the microprocessor is further programmed to store a desired threshold pressure value and to output a compressor activation signal when the pressure in the storage tank sensed by the pneumatic pressure sensor falls below the desired threshold pressure value.

2. The exoskeleton of claim 1, further comprising a first trimmer for adjusting the threshold voltage.

3. The exoskeleton of claim 2, further comprising a second trimmer for adjusting the delay period.

4. The exoskeleton of claim 3, further comprising a voltage divider for biasing the amplified EMG signal to be entirely a positive voltage.

5. The exoskeleton of claim 4, further comprising a low pass filter that filters out high frequency noise in the amplified EMG signal.

6. The exoskeleton of claim 5, further comprising a third trimmer for adjusting a centerline voltage that represents a voltage of a muscle at rest.

7. The exoskeleton of claim 6, wherein the first trimmer, second trimmer, and third trimmer comprise potentiometers that can be adjusted manually by a user.

8. The exoskeleton of claim 7, wherein the compressor is configured to refill the volume of two triggered pneumatic actuators in about one second.

* * * * *